United States Patent [19]

Pace et al.

[11] Patent Number: 5,284,568
[45] Date of Patent: Feb. 8, 1994

[54] DISPOSABLE CARTRIDGE FOR ION SELECTIVE ELECTRODE SENSORS

[75] Inventors: Salvatore J. Pace, Wilmington, Del.; James D. Hamerslag, West Chester, Pa.

[73] Assignee: E. I. Du Pont de Nemours and Company, Wilmington, Del.

[21] Appl. No.: 916,231

[22] Filed: Jul. 17, 1992

[51] Int. Cl.⁵ .................................. G01N 27/26
[52] U.S. Cl. .......................... 204/403; 204/409; 204/412; 204/416; 422/82.03; 128/635
[58] Field of Search ............ 204/403, 409, 412, 416, 204/417, 418, 419; 422/82.03, 128, 635; 435/817

[56] References Cited

U.S. PATENT DOCUMENTS

| | | | |
|---|---|---|---|
| 4,786,394 | 11/1988 | Enzer et al. | 204/401 |
| 4,810,251 | 3/1989 | Träubel et al. | 8/94.23 |
| 4,871,439 | 10/1989 | Enzer et al. | 204/401 |
| 4,933,048 | 6/1990 | Lauks | 204/1.11 |
| 4,994,167 | 2/1991 | Shults et al. | 204/403 |
| 5,004,583 | 4/1991 | Guruswamy et al. | 422/58 |
| 5,018,527 | 5/1991 | Pfab et al. | 128/635 |

Primary Examiner—John Niebling
Assistant Examiner—Bruce F. Bell

[57] ABSTRACT

A readily disposable ion selective electrode assembly, free of onboard reagents, for use in analyzers has a reference element and plural sensor elements linearly positioned in parallel on a substrate. An elastomeric flow channel member containing two parallel grooves creates flow channels on the substrate above the elements. The substrate holds the elastomer in compression and is retained by snaps injection molded into a housing. Electrical contacts and leakfree fluidic connections are provided by spring loaded connectors through the housing. Reference and sample fluids are drawn through the respective flow channels and come together to form a liquid junction downstream from the sensor elements. Bubbles, that might otherwise cause erroneous results, are detected.

17 Claims, 8 Drawing Sheets

DISPOSABLE CARTRIDGE FOR ION SELECTIVE ELECTRODE SENSORS

FIELD OF THE INVENTION

This invention relates to a disposable cartridge for use with ion selective electrode sensors and more particularly to an ion selective electrode assembly positioned in a cartridge which can be readily replaced.

BACKGROUND OF THE INVENTION

In the field of clinical diagnostics, there exists a need for reliable, low cost devices, i.e., for the routine quantitative determination of electrolytes and certain metabolites in physiological fluids. For this purpose, ion selective electrodes (ISE) have routinely been applied in the clinical measurement of sodium, potassium, chloride and similar ions. Most ion selective devices on the market today have a limited lifetime in the sense that the materials of construction tend to deteriorate with use and time. For example, flow conduits become coated and clogged due to clotting, or coagulation, of protein. Also the ion sensing membranes tend to degrade in performance with time due to membrane poisoning by sample constituents or general loss of ionophore potency. Such electrodes typically require a high degree of maintenance. It is desirable, therefore, to be able to replace the ion selective electrodes simply and conveniently with a low cost assembly before performance deteriorates when the occasion or need arises. This is preferable to the substantial maintenance that would be otherwise required to achieve high operating efficiency and effectiveness.

Disposable solid state sensors possess significant advantages over ion selective electrodes of conventional design. The ability to discard the sensor after each or several uses is highly desirable. A number of the sensor designs described in the prior art have sought to achieve this end result.

U.S. Pat. No. 4,994,167, issued to Schults et al., discloses a device in which a removable cartridge protects a membrane of an electrode assembly. However, the design does not define flow channels and also does not provide a particularly good seal, thus the unit is incapable of being used for analyzing multiple ions.

Another United States patent, issued to Pfab et al, U.S. Pat. No. 5,018,527, describes a complex flow system having multiple solid state membrane sensors, but the sensors are complex and difficult to manufacture.

In United States patent issued to Calzi, U.S. Pat. No. 4,966,670, an apparatus is provided for the differential measurement of electrolytes using a conventional ISE design. Unfortunately, the apparatus described uses bored channels disposed within a relatively large mounting block. This makes the device relatively expensive and requires relatively large volumes of sample and calibration solutions to operate. The need of present day sensors is that they efficiently operate with relatively small reagent volumes and they should be of low cost so that it is feasible to make them easily and they are readily replaceable. U.S. Pat. No. 4,871,439 issued to Enzer et al. incorporates a plurality of solid state electrodes in a disposable cartridge. The cartridge includes calibration solutions in self contained containers, a reference electrode fluid container and a container for spent fluids. These subassemblies are all integrated into a single structure. The whole unit is disposable but represents a relatively expensive, complex unit that is not suitable for the low cost testing large numbers of samples.

Finally, U.S. Pat. No. 4,786,394 Enzer et al. disclose a clinical analyzer which comprises a disposable cartridge containing sensors and further describes an electrically connected plug-in contained within the disposable cartridge, described previously, which contains bags for reagents, calibrators, waste dispose, etc.

SUMMARY OF THE INVENTION

The disadvantages of the ion selective electrode containing devices described in the foregoing prior art are substantially overcome by the disposable cartridge of the present invention. The invention is a disposable cartridge or sensor assembly for use in an analyzer, said assembly comprising: a substrate having a face with a reference element and plural sensor elements formed thereon, an electrical contact positioned on the substrate face for each element, a flow channel member having first and second opposed faces, the first face defining a pair of grooves positioned respectively over the substrate reference and sensor elements and joined together at one end of each groove, thereby defining liquid flow channels, the flow channel member defining orifices interconnecting the opposed faces at the one groove end and at each other groove end, and a housing having a wall and means for holding the substrate relative to the wall to compress the flow channel member therebetween, whereby the liquid flow channels are leak free, the wall defining ports for providing access to the flow channel member orifices and the substrate electrical contacts, said analyzer having a receptacle to removably receive the assembly, electrical connectors to operatively engage the substrate electrical contacts, and liquid connectors adapted to operatively engage and apply liquids to and from the flow channel member orifices.

In an improved embodiment of the invention, the flow channel member is elastomeric and the flow channel member second face has ribs transversely disposed relative to the defined channels for maintaining the integrity of the channels. Preferably the housing holding means includes side walls on the housing, the walls having snaps positioned to retain the substrate. In one embodiment, the flow channel member second face defines a cavity and the housing walls have ribs positioned to engage the cavity, thereby to position the flow channel member in the housing.

The disposable assembly described is a low cost assembly that can be easily replaced. The assembly is relatively leak free.

BRIEF DESCRIPTION OF THE DRAWING

The invention will be more fully understood from the following detailed description, taken in connection with the accompanying drawings, which form a part of this application and in which.

DETAILED DESCRIPTION OF THE INVENTION

Figure 1:
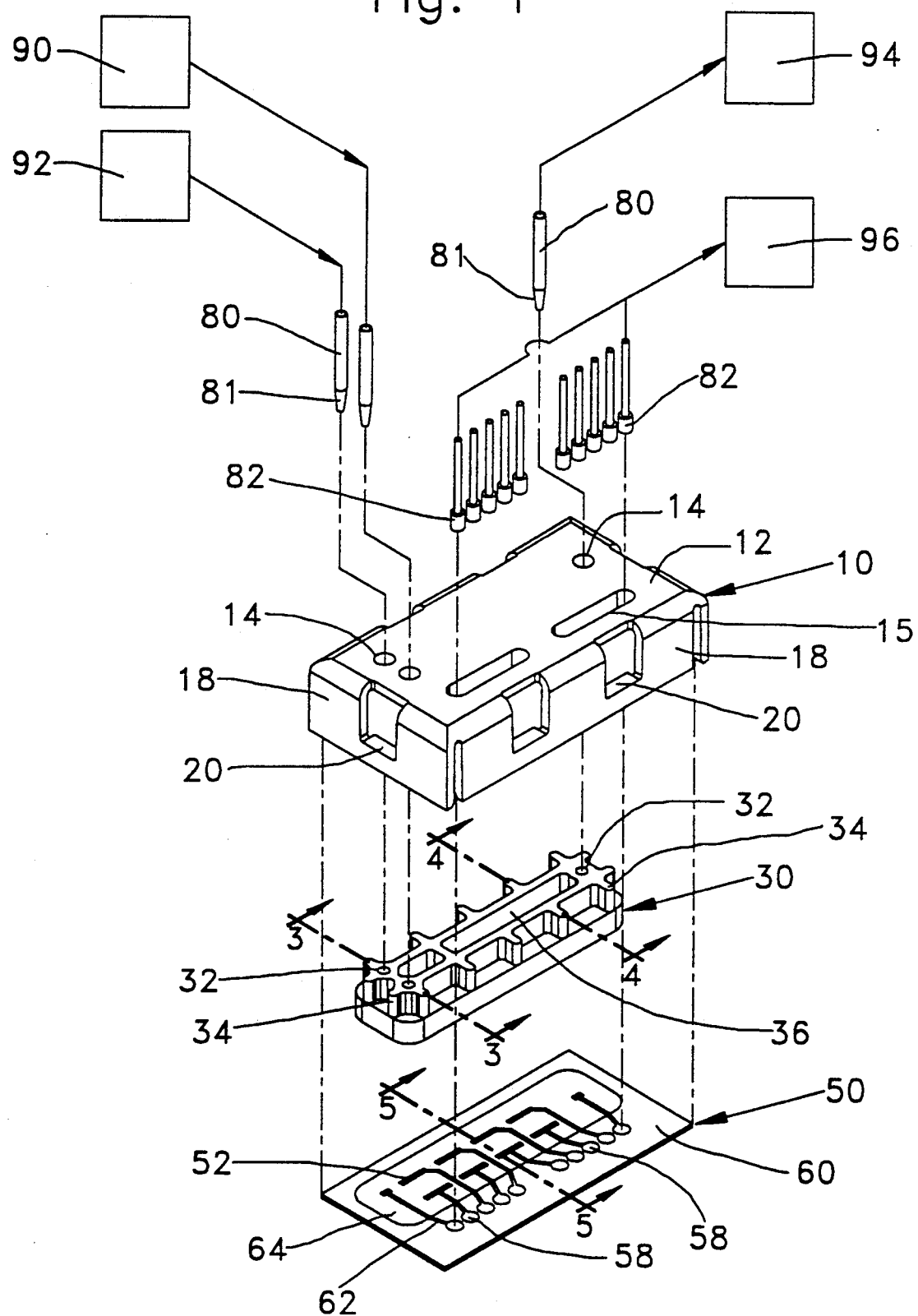
FIG. 1 is an exploded view of the sensor cartridge with fluid and electrical connections as viewed from the top.
Figure 2:
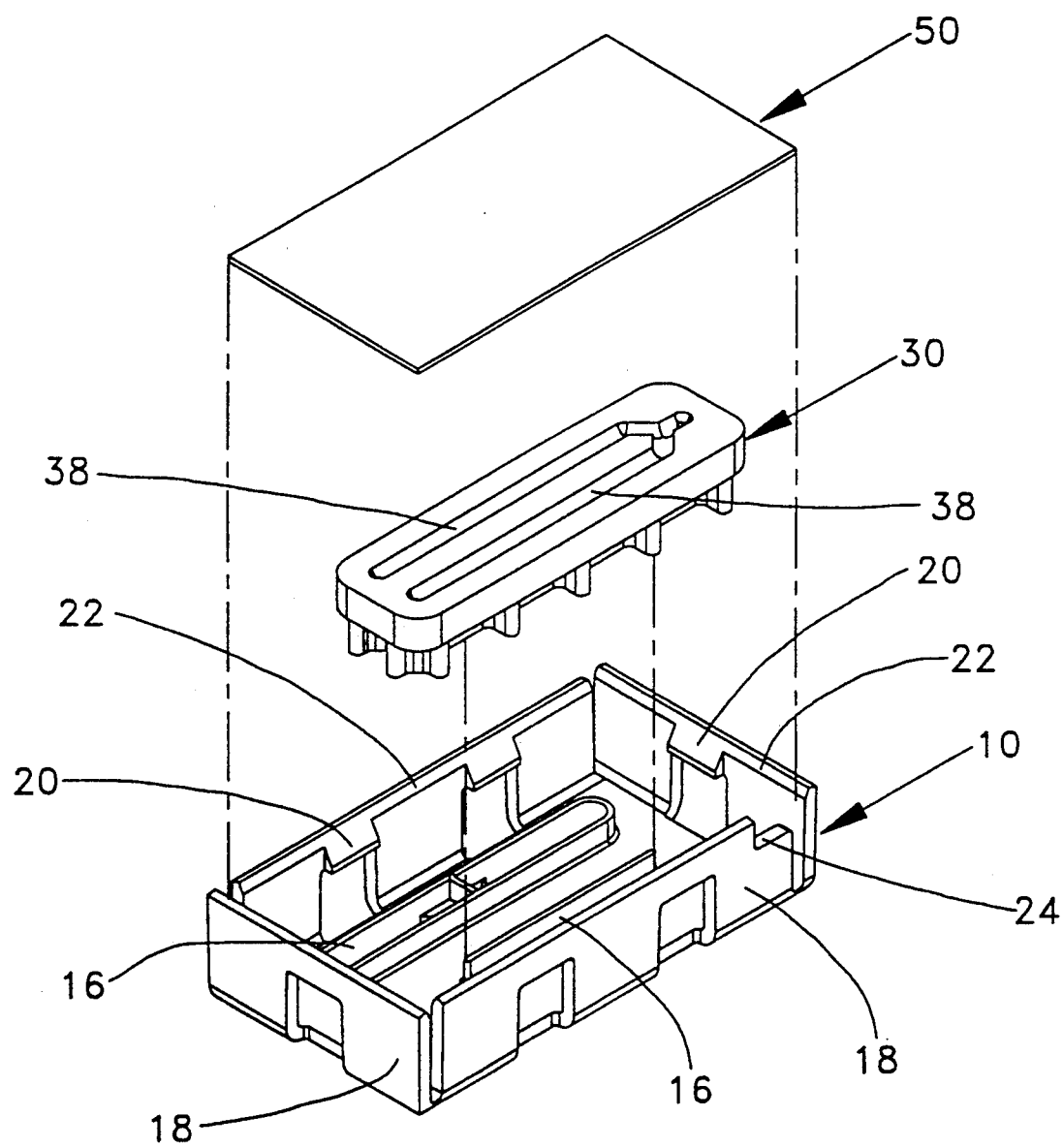
FIG. 2 is an exploded view of the sensor cartridge as viewed from the bottom.
Figure 7:
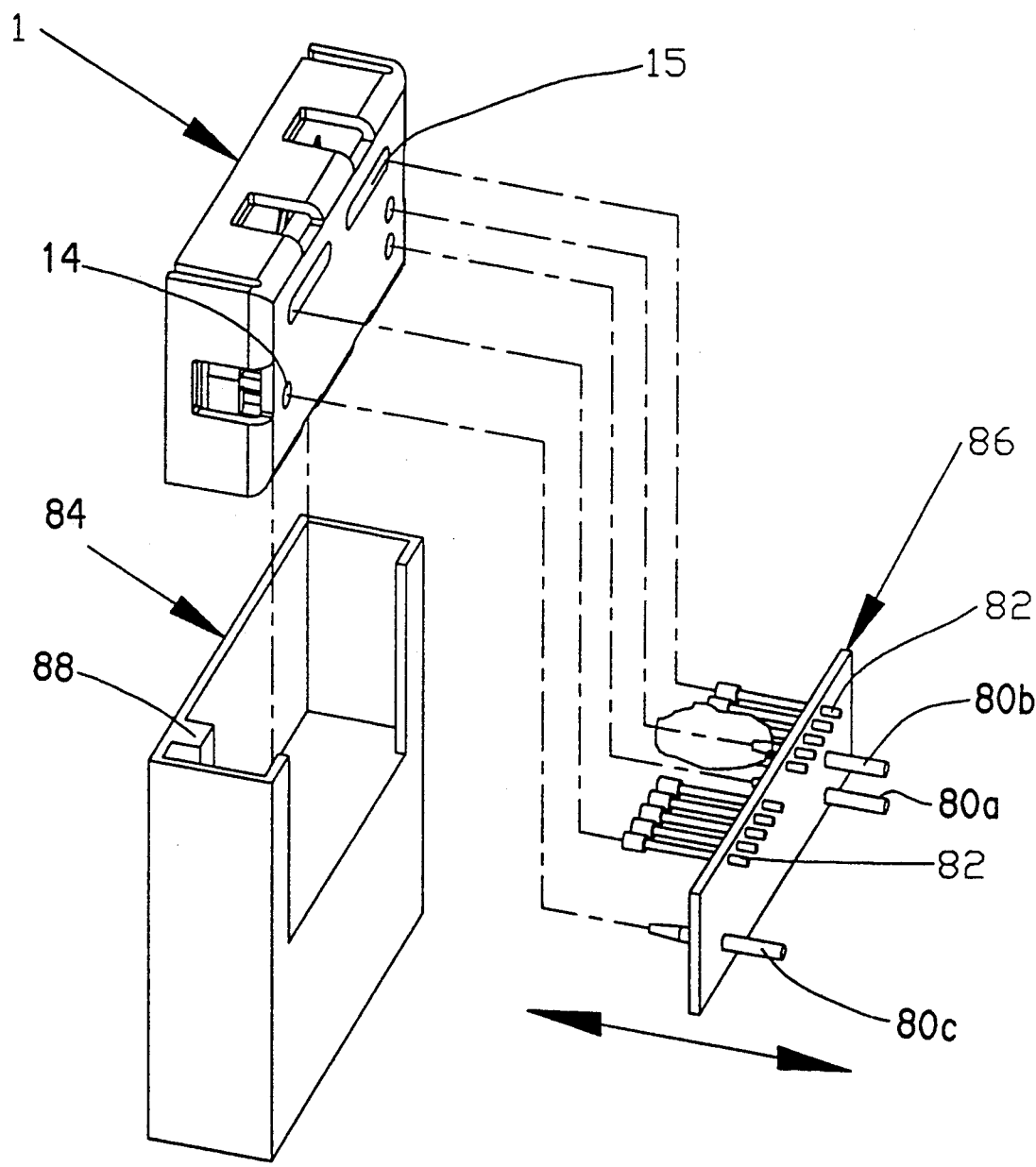
FIG. 7 is an exploded view of the sensor cartridge and a portion of the analyzer.
Figure 8:
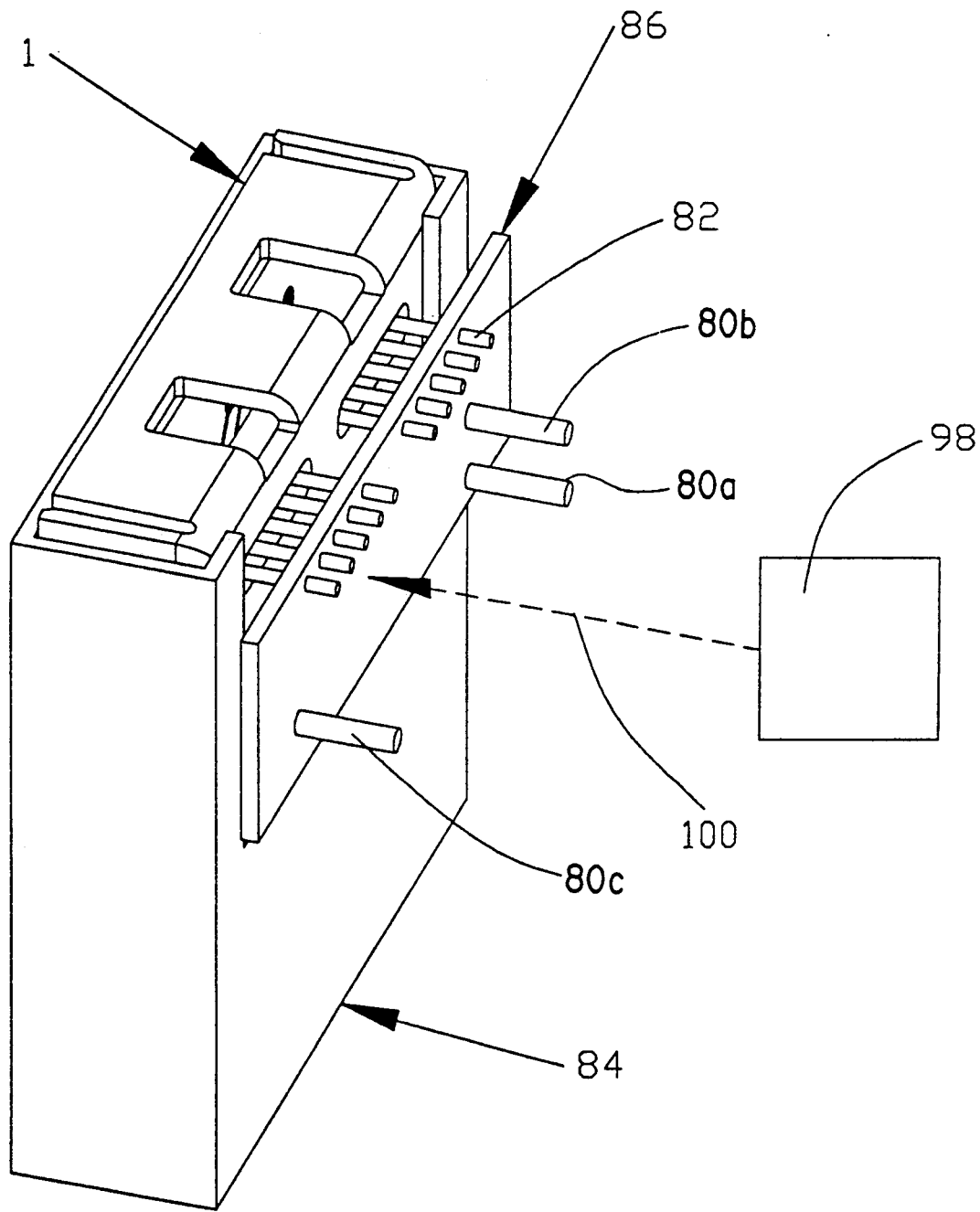
FIG. 8 is a perspective view of the sensor cartridge installed in a portion of the analyzer.

Referring to FIGS. 1, 2 and 7, a disposable sensor assembly or cartridge 1 is comprised of a housing 10, a flow channel member 30 and a sensor substrate 50. The size of the sensor cartridge 1 is such that it can be easily handled by the user and can be inserted into a sensor cartridge receptacle 84 (FIG. 8) of an analyzer of conventional design. Such analyzer may include an electrometer for amplifying the differential signals (measuring the potential difference) derived from the reference, sensor and ground elements of the ion sensor substrate, as will be described. The structure and assembly of these components is discussed in detail below.

The housing 10 is boxlike in shape with one side open and is constructed of a material which is chosen to provide sufficient mechanical strength such to maintain the flow channel member 30 and the sensor substrate 50 in alignment and contact. It also must be flexible enough to bend without failure during assembly of the sensor cartridge 1. Thermoplastic materials such as polyoxymethylene, polyethylene, polypropylene, polycarbonate or polystyrene with room temperature properties of flexural modulus in the range of 650 to 3500 MPa and tensile strength in the range of 14 to 100 MPa are preferred.

The top 12 of the housing 10 has the same geometry as the sensor substrate 50, which will be described. In a preferred embodiment of this invention, the geometry is rectangular. Other configurations such as circular are possible. The sensor substrate 50 is a multilayer structure. This fabrication is typically accomplished using screen printing technology as described by Pace in U.S. Pat. No. 4,454,007. This sensor substrate 50 includes a substrate 60 (FIG. 5) which may be a material chosen to be structurally rigid such that it exhibits negligible distortion when pressure is applied to it from the flow channel member, as will be described. The substrate should be an electrical insulator and provide support for layers 62, 64, 66 and 68 of a multilayer ion sensor. Acceptable materials for the substrate 60 are alumina, glass, glass-epoxy composites, polyester, polyethylene, polyimides, polystyrene or polycarbonate with alumina being preferred.

The sensor substrate 50 is created as described by Pace and others using any accepted multilayer ion sensor construction techniques. By way of example, one first deposits a conductor layer 62, then a dielectric layer 64, an interfacial layer 66 and finally the sensor membrane 68. Since these items are all well known in the art, they need not be described further and are fully described, for example, in the Pace patent whose disclosure is incorporated herein by reference. The sensing elements 52, which are comprised of the layers 62, 64, 66 and 68 (FIG. 5), may generally be disposed in banks or rows of linearly disposed sensor elements 52 (FIG. 1) with the sensor elements performing a reference function being on one side or row and the sensor elements performing a detecting or measuring function for the analyte on the other side or row. A ground element 54, which may be in the form of a printed silver layer or other suitable metal electrode, is formed at the end of the parallel banks of sensor elements 52. Similarly a bubble sensing element 56, which is in the form of an electrically conductive metal electrode of suitable materials such as silver, is provided at the beginning or entrance of each row of sensing elements 52.

Each of the sensing elements 52, ground element 54 and the bubble sensing element 56 are individually connected by electrically conductive paths which extend beyond the dielectric layer 64 to respective electrical contacts 58 which are formed on the top of the substrate 60. These contacts are located outside of the region that will be occupied by the flow channel member 30 which will form channels over the respective sensing elements as will be described. These contacts are positioned so that they may be contacted by electrical connectors 82, as will be described.

The flow channel member 30 is positioned above the sensor substrate 50. It has two faces, the lower face (best seen in FIG. 2) having defined therein a pair of grooves 38, which are spaced so as to be able to cover the respective elements 52, 54 and 56 on the substrate 60, thereby defining flow channels 70. The grooves should be small to reduce the fluid volume required. Typically grooves of 0.5 mm to 4 mm in diameter have been found suitable, although these numbers are not critical. The ends of the grooves 38 adjacent the ground element 54 of the substrate 60 are brought together to make a common exit point for the channels 70 that are defined by the grooves 38. Ports 32 are formed transversely through the thickness of the flow channel member 30 and are located such that one port 32 is at the common exit of the grooves and a separate port 32 is at the entrance of each of the grooves 38. This may best be seen in FIG. 1. The upper surface of the flow channel member is provided with support ribs 34 which aids in compressing the flow channel member against the sensor substrates 50, as will be described, to form the channels over the sensing elements without destroying the integrity of the channels 70. Furthermore, a rib receptacle 36 is provided to engage ribs 16 in the housing 10. These ribs 16 properly locate and position the flow channel member 30 relative to the sensing elements 52 and add to the stiffness of the housing 1.

The flow channel member 30 is formed of a material which is chosen to be chemically inert with respect to solutions likely to be used in the sensor cartridge. Its mechanical properties are such that it remains in a compressive state when assembled in the cartridge 1 and provides a leak-tight seal between it and the sensor substrate 60. It also provides a leak-tight seal between it and the fluid connectors 80. Elastomer materials such as butyl rubber, halobutyl rubber, bromobutyl rubber, silicone, polyurethane or polyvinyl chloride with room temperatures mechanical properties of hardness in the range of 40 Shore A (ASTM D-2240) to 60 Shore A and a segment modulus at 10% strain in the range 0.7 to 4.2 MPa are preferred.

The top 12 of the housing 10 contains apertures or holes 14 to permit fluid connections and ports or apertures 15 to accommodate electrical connection to the sensor cartridge 1. Side walls 18 of the housing have snaps 20 which protrude to retain the sensor substrate 50 in the sensor cartridge 1 in the embodiment of this invention depicted. The side walls 18 are independent of each other to facilitate bending during assembly. Portions of the housing side walls may be cut out to accommodate the molding operation as necessary. Furthermore the apertures 15 for the electrical connectors may be reinforced on the bottom side of the housing by ribs 25.

The electrical connectors 82 are connected to electronic circuitry 96 which may as needed incorporate a multiplexer and electrometer amplifiers to selectively connect to the various pairs of sensing elements 52, ground elements 54 and bubble sensing element 56 so as to facilitate the various differential and bubble to ground measurements necessary for the operation of the device. The outlet of the flow channel 14C is connected through fluid connector 80C to a waste receptacle 94. Fluid flow may be facilitated by means of a pump (not shown). Similarly a source of sample fluid 92 to be tested and/or calibrator fluid is coupled through a fluid connector 80a, through port 14a to the sample port 32a of the flow channel member 30 to feed the sensor channel 70a. A source of reference fluid 90 may be connected through a second fluid.. connector 80b and the reference port 14b to sample port 32b of to the flow channel member 30 to feed the reference channel 70.

The sensor cartridge 1 is assembled by first placing the rib receptacle 36 of the flow channel member 30 over the rib 16 of the housing 10. This positions and defines the location of the flow channel member 30 with respect to the housing 10. The sensor substrate is then placed on the tapered portion 22 of the housing side walls 18. This helps to define the location of the sensor substrate 50 with respect to the housing 10, thereby locating the flow channel member 30 to the sensor substrate 50. A force is applied to the sensor substrate 50 manually or by an assembly tool causing the housing side walls 18 to bend outward and the flow channel member 30 to be compressed. After the sensor substrate 50 has been moved passed the snap 20, the housing side walls 18 bend back to their original position.

Figure 5:
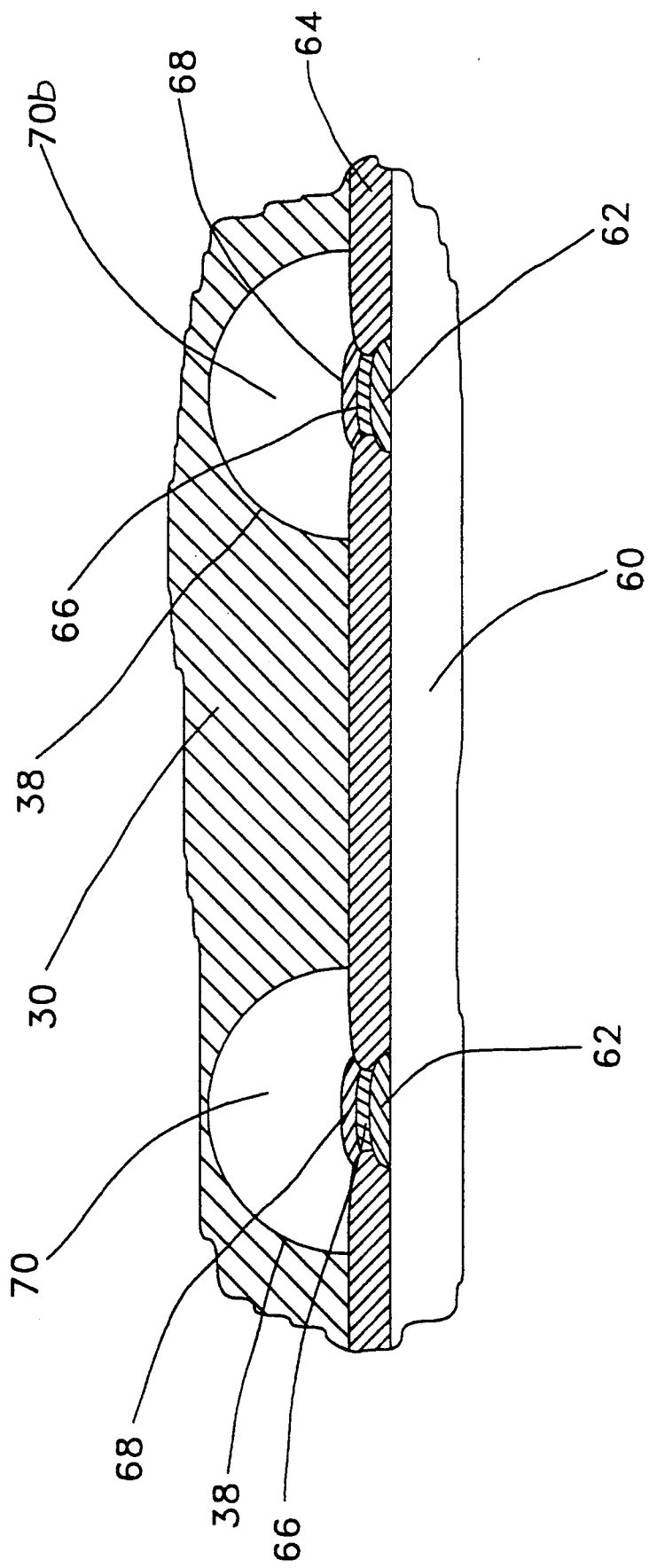
FIG. 5 is a section view taken of an assembled sensor cartridge on line 5—5 in FIG. 1.

The compressive state of the flow channel member 30 between the sensor substrate 50 and the housing 10 keeps the sensor cartridge 1 assembled. This compressive state of the flow channel member 30 also maintains the leak-free interface between the flow channel member 30 and the sensor substrate 50. As seen in FIG. 5, when the sensor cartridge 1 is assembled, the groove 38 and the sensor substrate 50 define the flow channels 70a and 70b.

The sensor cartridge 1 is positioned into a sensor cartridge receptacle 84 (FIGS. 7 and 8) of analyzer. The analyzer incorporates the source of reference sample and calibrator fluids and contains the waste receptacle and electronic circuitry necessary to make the necessary measurements of the differential voltages across the ion sensitive electrodes. Since reagent containers and sampling devices for supplying these fluids and making these measurements are standard, they need not be described. The correct orientation of the cartridge 1 is guaranteed by the housing sidewall cutout 24 (FIG. 2) and the protrusion 88 of the sensor cartridge receptacle 84. The preferred orientation is such that the electrical connectors 82 are located above the fluid connectors 80a, 80b, and 80c. This arrangement minimizes fluid contact to the electrical connectors 82 if there is leakage from the fluid connectors 80a, 80b, and 80c. The analyzer connector plate 86 is then translated to make fluid and electrical connection to the sensor cartridge 1.

Figure 3:
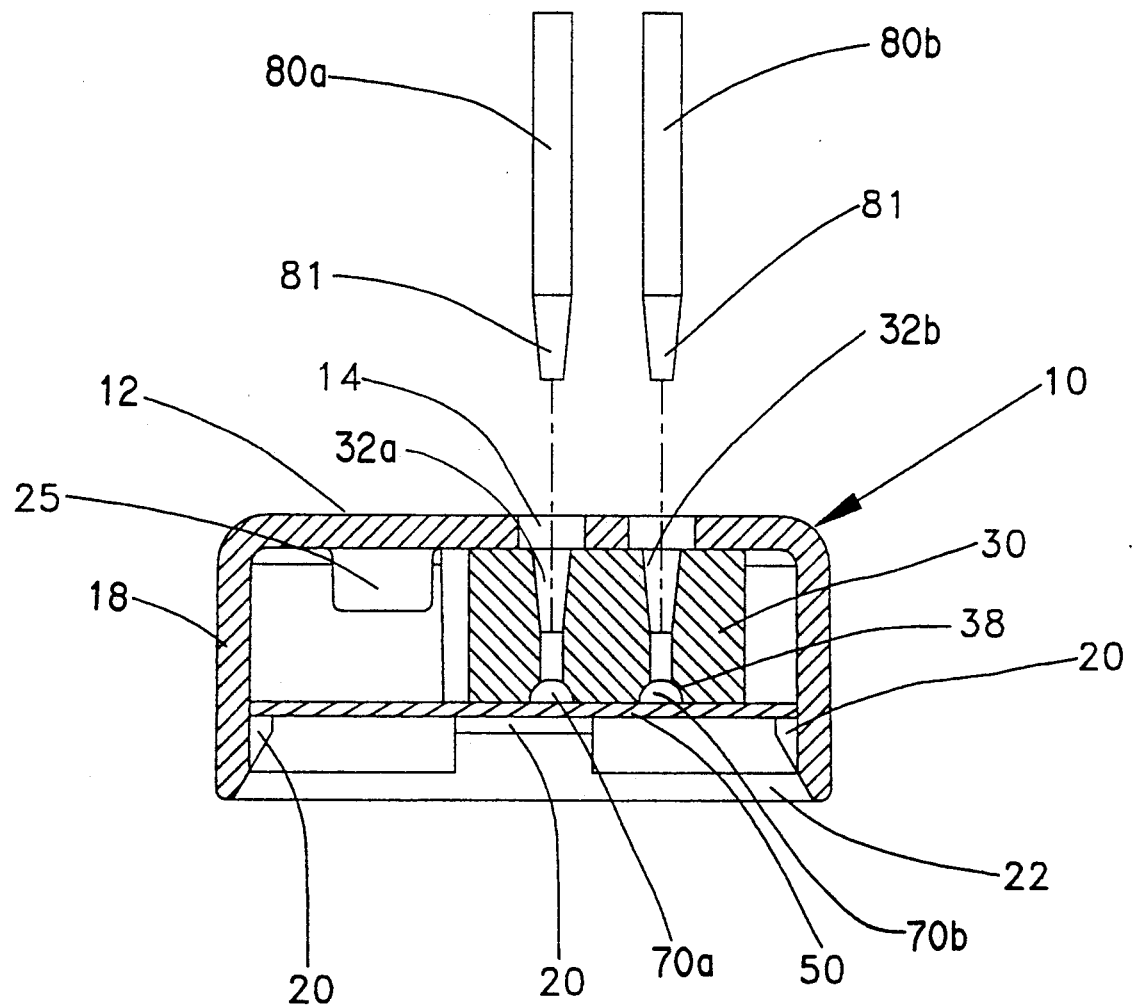
FIG. 3 a sectional view of an assembled sensor cartridge taken on line 3—3 in FIG. 1.
Figure 4:
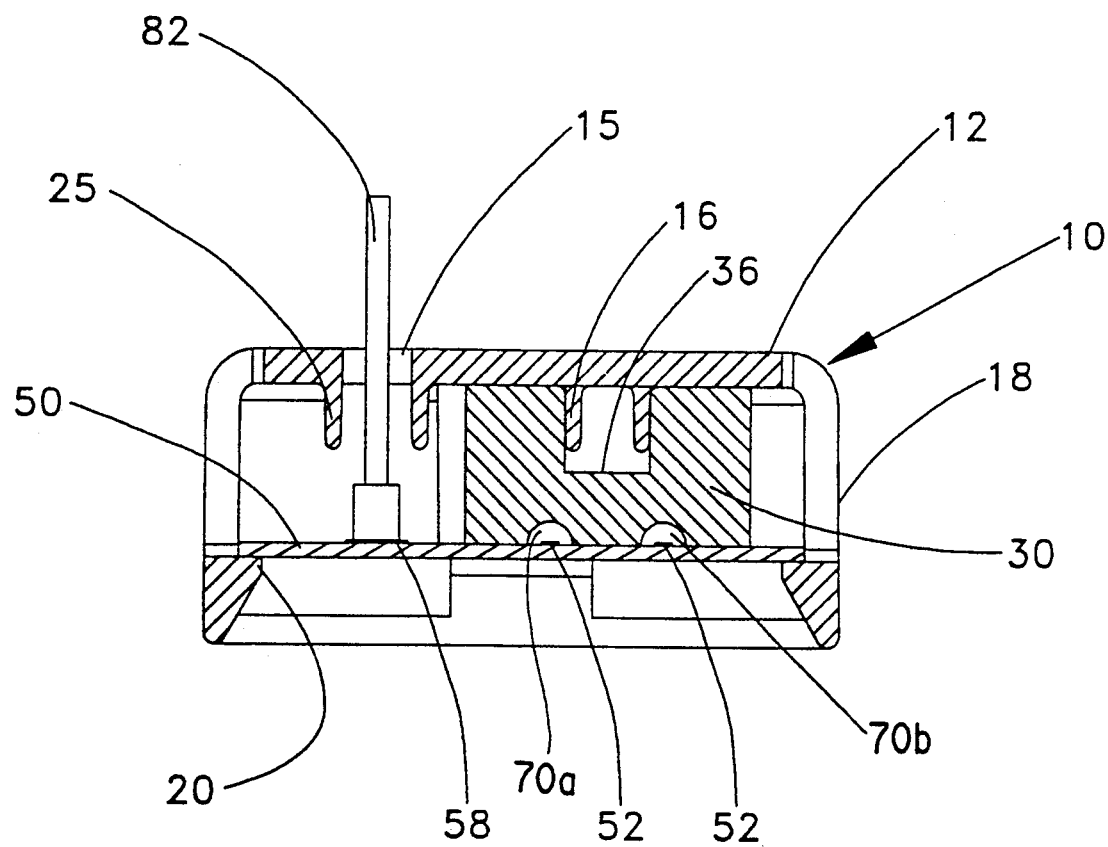
FIG. 4 is a sectional view taken of an assembled sensor cartridge on line 4—4 in FIG. 1.

Referring to FIG. 3, the ports 32a and 32b are expanded when the fluid connectors 80a and 80b are translated into the flow channel member 30, thus creating a leak free interface. The tapered ends 81 of the fluid connectors 80a and 80b facilitates this connection but is not required. The electrical connector 82 (FIG. 4) contacts the electrical contacts 58 (FIG. 1) of the sensor substrate 50.

Figure 6:
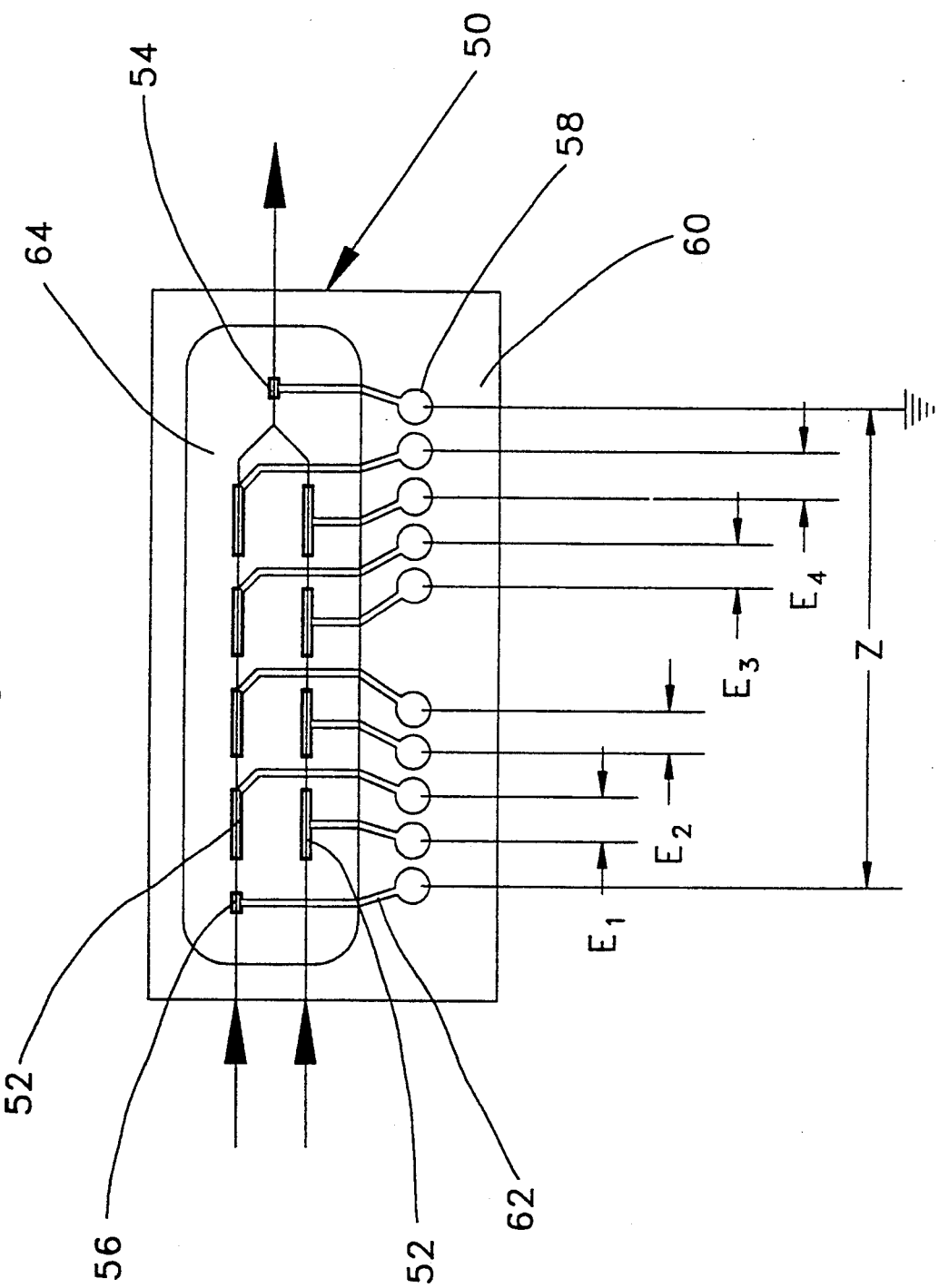
FIG. 6 is a schematic diagram of the sensor substrate.

Operation of the sensor cartridge 1 consists of a two point calibration and then multiple sample measurements. Both the two point calibration and the sample measurement are comprised of two measurements. Referring to FIGS. 1, 5 and 6, all fluids are drawn into the system by way of a pump (not shown) located preferably on the waste 94 side of the sensor cartridge 1. Flow from the ports 90 and 92 is controlled by pinch valves (not shown). Reference fluids are solutions with known ionic concentrations over the range to be measured.

The first part of the two point calibration consists of drawing a reference fluid by way of the reference port 90 into the flow channel 70b and then drawing the same reference fluid by way of the sample port 92 into the flow channel 70a. A potential $E_i$ (FIG. 6) is then measured by the electronics 96. The second part of the two point calibration consists of pumping a different reference fluid by way of the sample port 92 into the flow channel 70a. A potential $E_i$ (FIG. 6) is then measured by the electronics 96. The response or slope of the sensor is calculated from the measured potentials and the known ionic concentrations of the reference fluids determined earlier.

The first part of the sample measurement consists of pumping a reference fluid by way of the reference port 90 into the flow channel 70b and then drawing the same reference fluid by way of the sample port 92 into the flow channel 70a. A potential $E_i$ (FIG. 6) is then measured by the electronics 96. The second part of the sample measurement consists of drawing the sample fluid by way of the sample port 92 into the flow channel 70a. A potential $E_i$ (FIG. 6) is then measured by the electronics 96. The concentration of the ion in the sample is calculated from the measured potentials and the known slope of the sensor and ionic concentration of the reference fluid.

Streaming potentials caused by fluid flow are minimized by the ground element 54. The presence of air bubbles in the flow channel 70a and 70b between the bubble sensing element 56 and the ground element 54 can be determined by measuring the impedance Z (FIG. 6) of the fluid between these elements.

As used in this specification, the term "fluid" includes liquids as well as gases, although at the present time liquids are primarily used. Also, although several reference sensor elements are shown, a single element can be used. The sensor elements may be along a curved path if desired.

The sensor cartridge just described is seen to provide a low cost, reliable disposable unit that can replace a unit in use whenever or before it fails. The unit provides a leak-free seal with the sensor substrate and leak-free fluidics. It is designed to maintain critically aligned flow paths for providing channels for the sensing elements.

What is claimed is:

1. A disposable sensor assembly for use in an analyzer, said assembly comprising:
 a substrate having a face with a reference element and plural sensor elements formed thereon,
 an electrical contact positioned on the substrate face for each element,
 a flow channel member having first and second opposed faces, the first face defining a pair of grooves positioned respectively over the substrate reference and sensor elements and joined together at one end of each groove, thereby defining liquid flow channels, the flow channel member defining orifices interconnecting the opposed faces at the one groove end and at each other groove end, and a housing having a wall and means for holding the substrate relative to the wall to compress the flow channel member therebetween, whereby the liquid flow channels are leak-free, the wall defining ports for providing access to the flow channel member orifices and the substrate electrical contacts, said analyzer having a receptacle to removably receive the assembly, electrical connectors to operatively engage the substrate electrical contacts, and liquid connectors adapted to operatively engage and apply liquids to and from the flow channel member orifices.

2. An assembly as set forth in claim 1 wherein the housing holding means includes side walls on the housing, the walls having snaps positioned to retain the substrate in a substantially leak free manner.

3. An assembly as set forth in claim 2 wherein the flow channel member is elastomeric.

4. An assembly as set forth in claim 3 wherein the flow channel member second face has ribs transversely disposed relative to the defined channels for maintaining integrity of the channels.

5. An assembly as set forth in claim 4 wherein the flow channel member second face defines a cavity, and the housing wall has ribs positioned to engage the cavity, thereby to position the flow channel member in the housing.

6. An assembly as set forth in claim 2 wherein the flow channel member second face defines a cavity, and the housing wall has ribs positioned to engage the flow channel member cavity, thereby to position the flow channel member in the housing.

7. An assembly as set forth in claim 1 wherein the flow channel member second face defines a cavity, and the housing wall has ribs positioned to engage the flow channel member cavity, thereby to position the flow channel member in the housing.

8. An assembly as set forth in claim 5 wherein the substrate face has a ground element positioned at the junction of the channels in the flow channel member and an electrical contact therefore positioned away from the flow channel member.

9. An assembly as set forth in claim 4 wherein the substrate face has a ground element positioned to be at the junction of the channels in the flow channel member and an electrical contact therefore positioned away from the flow channel member.

10. An assembly as set forth in claim 8 wherein the substrate face has a bubble sensing element positioned to be in one of the flow channel member defined channels.

11. An assembly as set forth in claim 10 wherein analyzer includes electronic circuitry connected to the pins for measuring electrical signals provided by the sensing elements.

12. An assembly as set forth in claim 1 wherein the flow channel member is elastomeric.

13. An assembly as set forth in claim 12 wherein the analyzer includes means for introducing liquid to be analyzed to one of the fluid connectors.

14. A disposable sensor assembly for use in an analyzer, said assembly comprising:

a substrate having a face with a linearly disposed reference element and plural sensor elements formed thereon, an electrical contact positioned on the substrate face for each element, a flow channel member having first and second opposed faces, the first face defining a pair of grooves positioned respectively over the substrate reference and sensor elements and joined together at one end of each groove, thereby defining liquid flow channels, the flow channel member defining orifices interconnecting the opposed faces at the one groove end and at each other groove end, and a housing having a wall and means for holding the substrate relative to the wall to compress the flow channel member therebetween, whereby the flow channels are leak free, the wall defining ports for providing access to the flow channel member orifices and the substrate electrical contacts.

15. An assembly as set forth in claim 14 wherein the housing holding means includes side walls on the housing, the walls having snaps positioned to retain the substrate.

16. An assembly as set forth in claim 14 wherein the flow channel member second face has ribs transversely disposed relative to the defined channels for maintaining integrity of the channels.

17. An assembly as set forth in claim 14 wherein the flow channel member second face defines a cavity, and the housing wall has ribs positioned to engage the flow channel member cavity, thereby to position the flow channel member in the housing.

* * * * *

UNITED STATES PATENT AND TRADEMARK OFFICE
CERTIFICATE OF CORRECTION

PATENT NO. : 5,284,568

DATED : February 8, 1994

INVENTOR(S) : Salvatore J. Pace, James D. Hamerslag

It is certified that error appears in the above—identified patent and that said Letters Patent is hereby corrected as shown below:

On the title page:
In [75] Inventors: Please correct as follows:

(1) James D. Hamerslag
      (2) Salvatore J. Pace

Signed and Sealed this

Twenty-fifth Day of October, 1994

Attest:

BRUCE LEHMAN

Attesting Officer     Commissioner of Patents and Trademarks